United States Patent
De Witte et al.

(10) Patent No.: US 6,242,440 B1
(45) Date of Patent: Jun. 5, 2001

(54) SYNERGISTIC COMPOSITIONS COMPRISING AN OXATHIAZINE AND A BENZOTHIOPHENE-2-CARBOXAMIDE-S,S-DIOXIDE

(75) Inventors: Ludo Antoinnette De Witte, Merksplas; Alex Raymond Albert Valcke, Wechelderzande; Mark Arthur Josepha Van der Flaas, Herselt; Willy Modest Louisa Willems, Lille, all of (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/529,271

(22) PCT Filed: Oct. 7, 1998

(86) PCT No.: PCT/EP98/06495

§ 371 Date: Apr. 10, 2000

§ 102(e) Date: Apr. 10, 2000

(87) PCT Pub. No.: WO99/18795

PCT Pub. Date: Apr. 22, 1999

(30) Foreign Application Priority Data

Oct. 15, 1997 (EP) .................................................. 97203227

(51) Int. Cl.⁷ .................................................. A61K 31/54
(52) U.S. Cl. .................................. 514/222.5; 514/222.8; 514/223.2; 514/223.5
(58) Field of Search .................. 514/272, 222.5, 514/222.8, 223.2, 223.5

(56) References Cited

U.S. PATENT DOCUMENTS

| 4,569,690 | 2/1986 | Brouwer et al. | 71/90 |
| 5,244,893 | 9/1993 | Elbe et al. | 514/212 |
| 5,622,546 | 4/1997 | Elbe et al. | 106/18.33 |
| 5,777,110 | * 7/1998 | Davis et al. | 544/2 |

FOREIGN PATENT DOCUMENTS

| 195 48 873 | * 7/1997 | (DE) . |
| 8-012504 | * 1/1996 | (JP) . |
| WO 95/05739 | 3/1995 | (WO) . |
| WO 95/06043 | 3/1995 | (WO) . |

OTHER PUBLICATIONS

English translation of DE 195 48 873.

* cited by examiner

*Primary Examiner*—Jose' G. Dees
*Assistant Examiner*—Alton Pryor

(57) ABSTRACT

This invention relates to synergistic compositions of oxathiazines and benzothiophene-2-carboxamide-S,S-dioxides for use as fungicidal preservatives in the protection of materials, such as protection of wood, wood products, biodegradable materials and coatings.

8 Claims, No Drawings

SYNERGISTIC COMPOSITIONS COMPRISING AN OXATHIAZINE AND A BENZOTHIOPHENE-2-CARBOXAMIDE-S,S-DIOXIDE

This application is a 371 of 00/006,495 filed Oct. 7, 1998.

CROSS REFERENCE TO RELATED APPLICATIONS

This application is the national stage of application no. PCT/EP98/06495, filed Oct. 7, 1998 which application claims priority from EP 97203227.0, filed Oct. 15, 1997.

This invention relates to synergistic compositions of oxathiazines and benzothiophene-2-carboxamide-S,S-dioxides for use as fungicidal preservatives in tie protection of materials, such as protection of wood, wood products, biodegradable materials and coatings.

It now has been found that compositions comprising particular ratios of an oxathiazine of formula (I) and a benzotihiophene-2-carboxamide-S,Sdioxide of formula (II) exhibit synergistic fungicidal activity.

The present invention is concerned with compositions comprising an oxathiazine of formula (I), or a salt thereof, and a benzothiophene-2-carboxamide-S,S-dioxide of formula (II), or a salt thereof, in quantities producing a mutual synergistic effect, and a carrier.

The oxathiazines of formula (I) have the following structure

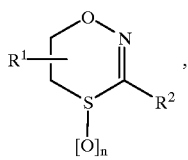

(I)

wherein n is 0, 1 or 2; $R^1$ is hydrogen, $C_{1-4}$alkyl or benzyl; and $R^2$ represents (a) phenyl; phenyl substituted with 1 to 3 substituents independently selected from hydroxyl, halo, $C_{1-12}$alkyl, $C_{5-6}$cycloaLkyl, trihalomethyl, phenyl, $C_{1-5}$alkoxy, $C_{1-5}$alkylthio, tetrahydropyranyloxy, phenoxy, $C_{1-5}$alkycarbonyl, phenylcarbonyl, $C_{1-4}$alkylsuifinyl, $C_{1-4}$alkylsulfonyl, carboxy or its alkali metal salt, $C_{1-5}$alkyloxy-carbonyl, $C_{1-5}$alkylaminocarbonyl, phenylaminocarbonyl, tolylainocarbonyl, morpholinocarbonyl, amnino, nitro, cyano, dioxolanyl or $C_{1-4}$alkyloxyiminomethyl; naphthyl; pyridinyl; thienyl, preferably when n is not 2; furanyl; or thienyl or furanyl substituted with one to three substituents independently selected from $C_{1-4}$alkyl, $C_{1-4}$alkyloxy, $C_{1-4}$alkylthio, halo, cyano, formyl, acetyl, benzoyl, nitro, $C_{1-4}$alkyloxy-carbonyl, phenyl, phenylaminocarbonyl and $C_{1-4}$alkyloxyiminomethyl; or $R^2$ represents a radical of formula

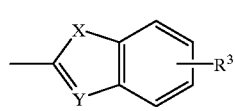

(b)

wherein X is oxygen or suilfr; Y is nitrogen or CH or $C(C_{1-4}$allyloxy); and $R^3$ is hydrogen or $C_{1-4}$akyl.

Said compounds of formula (I) are described in WO-95/06043, published on Mar. 2, 1995, as a bactericidal and fungicidal compounds useful in wood-protection. The use of said compounds for the protection of non-living materials, in particular the anti-fouling use, is described in WO-95/05739, published on Mar. 2, 1995. WO95/05739 also describes the antibacterial, anti-yeast, antifungal, algicidal, anti-crustacean and molluscicidal properties of said compounds of formula (I) and compositions comprising them.

All compounds of formula (I) can be prepared following the procedures described in U.S. Pat. No. 4,569,690.

The benzothiophene-2-carboxamide-S,S-dioxides of formula (II) can be represented by the formula

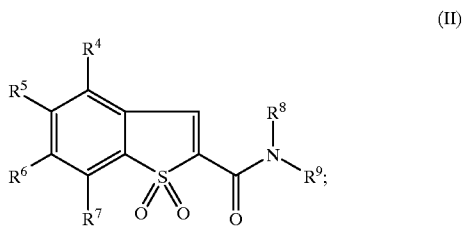

(II)

wherein $R^8$ represents straight-chain or branched alkyl having 1 to 20 carbon atoms, or represents in each case straight-chain or branched halogenoalkyl, cyanoalkyl, hydroxyalkyl, alkoxyalkyl or alkoxycarbonylalkyl, each of which has 1 to 8 carbon atoms in the individual alkyl moieties, or represents straight-chain or branched alkenyl having 2 to 12 carbon atoms, or represents straight-chain or branched alkynyl having 2 to 12 carbon atoms, or represents cycloalkylalkyl or cycloalkyl, each of which has 3 to 7 carbon atoms in the cycloalkyl moiety and, in the case of cycloalkylalkyl, 1 to 6 carbon atoms in the straight-chain or branched alkyl moiety, and each of which is optionally monosubstituted to hexasubstituted in the cycloalky moiety by identical or different substituents, suitable cycloalkyl substituents in each case being: halogen, in each case straight-chain or branched alkyl having 1 to 4 carbon atoms or in each case straight-chain or branched halogenoalkyl having 1 to 4 carbon atoms and 1 to 9 identical or different halogen atoms; furthermore represents arylalkyl, arylalkenyl, arylalyynyl or aryl, each of which has 6 or 10 carbon atoms in the aryl moiety and, in the cases of arylalkyl, arylalkenyl and arylalkynyl, up to 12 carbon atoms in the respective straight-chain or branched alkyl or alkenyl or alkynyl moiety, each of which is optionally monosubstituted to pentasubstituted in the aryl moiety by identical or different substituents, suitable aryl substituents in each case being: halogen, cyano, nitro, formylamido, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkyl-aminocarbonyl, alkylcarbonylamino, N-alkyl-alkylcarbonylamino, N-alkylformyl-carbonylamino or alkoximinoalkyl, each of which has 1 to 4 carbon atoms in the individual alkyl moieties, and phenyl which is optionally monosubstituted or polysubstituted by identical or different substituents from the group consisting of halogen and/ or straight-chain or branched aLkyl having 1 to 4 carbon atoms; $R^9$ represents hydrogen or straight-chain or branched alkyl which has 1 to 6 carbon atoms and which is optionally monosubstituted or polysubstituted by identical or different substituents, suitable substituents being: hydroxyl, halogen, cyano, and in each case straight-chain or branched alkoxy, alkoxycarbonyl or dialkylamino; each of which has 1 to 6 carbon atoms in the individual akyl moieties; or $R^8$ and $R^9$ together with the nitrogen atom to which they are bonded represent a saturated 5- to 7-membered heterocycle which is optionally monosubstituted or polysubstituted by identical or different substituents and which can optionally contain 1 or 2 further hetero atoms selected from the group consisting of nitrogen, oxygen and sulphur, suitable substituents in each case being: halogen, in each case straight-chain or branched alkyl, alkoxy or alkoxycarbonyl having in each case 1 to 4 carbon atoms or straight-chain or branched halogenoalkyl having 1 to 4 carbon atoms and 1 to 9 identical or different halogen atoms; and $R^4$, $R^5$, $R^6$ and $R^7$ independently of one another in each case represent hydrogen, halogen, cyano, nitro or in each case straight-chain or branched alkyl, alkoxy, alkylthio, halogenoalkyl, halogenoalkoxy or halogenoalkylthio each of which has 1 to 6 carbon atoms and, in the case of halogenoaLky, halogenoalkoxy or halogenoalkylthio, 1 to 13 identical or different halogen atoms.

Said compounds of formula (II), their preparation and use in plant protection, the protection of materials and in the field of human and veterinary medicine, are described in EP-0,512,349, published on Nov. 11, 1992.

All compounds of formula (II) can be prepared following the procedures described in EP-0,512,349.

In the foregoing definitions halo is generic to fluoro, chloro, bromo and iodo; $C_{1-4}$alkyl defines straight and branch chained saturated hydrocarbon radicals having from 1 to 4 carbon atoms comprising methyl, ethyl, n-propyl, 1-methylethyl, n-butyl, 1,1-dimethyl-ethyl, 1-methylpropyl, 2-methylpropyl; $C_{1-5}$alkyl includes $C_{1-4}$alkyl radicals as defined above and saturated hydrocarbon radicals having five carbon atoms, e.g. n-pentyl and the branched pentyl isomers; $C_{1-6}$alkyl includes $C_{1-5}$alkyl radicals as defined above and six carbon containing homologues, e.g. n-hexyl and the branched hexyl isomers; $C_{1-12}$alkyl includes $C_{1-6}$alkyl and saturated hydrocarbon radicals having from 7 to 12 carbon atoms, e.g. heptyl, octyl, nonyl, decyl, undecyl and their isomers. The term alkali metal cation in particular is a sodiurm or potassium cation. Trihalomethyl defines a methyl group being fully substituted with halo atoms, in particular trifluoromethyl and trichloromethyl. $C_{1-4}$alkyloxyiminomethyl defines a radical of formula —CH=N—O—$C_{1-4}$alkyl. $C_{5-6}$cycloalkyl comprises cyclopentyl and cyclohexyl.

Particular compounds of formula (I) for use in the method are those wherein n is 0, 1 or 2; $R^1$ is hydrogen, $C_{1-4}$alkyl or benzyl; and $R^2$ represents phenyl; naphthyl; pyridinyl; thienyl provided that n is not 2; furanyl optionally substituted with 1 to 3 substituents independently selected from $C_{1-4}$alkyl and $C_{1-4}$alkyloxycarbonyl; or phenyl substituted with 1 or 2 substituents independently selected from hydroxyl, halo, $C_{1-12}$alkyl, $C_{5-6}$cylo-alkyl, trihalomethyl, phenyl, $C_{1-5}$alkoxy, $C_{1-5}$alkylthio, tetrahydropyranyloxy, phenoxy, $C_{1-4}$alkylcarbonyl, phenylcarbonyl, $C_{1-4}$alkylsulfnyl, $C_{1-4}$alkylsulfonyl, carboxy or its alkali metal salt, $C_{1-4}$aakoxycarbonyl, $C_{1-4}$alkylaminocarbonyl, phenylaminocarbonyl, tolylaminocarbonyl, morpholinocarbonyl, amino, nitro, cyano, or dioxolanyl.

Of interest are those compounds of formula (I) wherein n is 1 and $R^2$ represents phenyl, thienyl or phenyl substituted with one or two substituents selected from halo and trihalomethyl; or those wherein n is 2 and $R^2$ represents phenyl or phenyl substituted with one or two substituents selected from halo and trihalomethyl.

Of further interest are the compounds of formula (I) wherein $R^1$ is hydrogen, n is 1 or 2, and $R^2$ represents phenyl, $C_{1-6}$alkylphenyl, halophenyl, dihalophenyl, biphenyl, $C_{1-5}$alkyloxyphenyl, trihalomethylphenyl, nitrophenyl, phenyl substituted with $C_{1-4}$alkyloxycarbonyl, $C_{1-6}$alkylnitrophenyl, unsubstitluted fiinyl or thienyl, or furanyl or thienyl substituted with ethoxycarbonyl, cyano, chlorine or bromine.

Of particular interest are the compounds of formula (1) wherein $R^1$ is hydrogen, n is 1 or 2, and $R^2$ represents 3-fluorophenyl, 4-chlorophenyl, 3,4-dichlorophenyl, 3,5-dichlorophenyl, 3-trifluoromethylphenyl, 4-trifluoromethylphenyl, 4-methylphenyl, 3-ethanonephenyl, 3-nitrophenyL 3-methyl-4-nitrophenyl or 2-thienyl.

Also of further interest are those compounds of formula (I) wherein $R^1$ is hydrogen, $R^2$ is a radical of formula (b) wherein X is sulfur, Y is nitrogen or CH, and $R^3$ is hydrogen.

The most preferred compound of formula (I) is 3-(benzo[b]thien-2-yl)-5,6-dihydro-1,4,2-oxathiazine, 4-oxide, generically known as "bethoxazin", and referred to as "compound (1)" throughout the description, having formula:

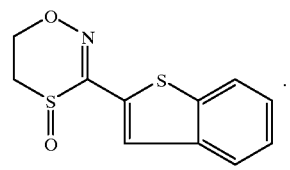

(1)

Particular compounds of formula (II) are those compounds of formula (II) wherein wherein $R^8$ represents methyl, ethyl, n- or i-propyl, n-, i-, s- or t-butyl, n- or i-pentyl, 20 n- or i-hexyl, n- or i-heptyl, n- or i-octyl, n- or i-nonyl, n- or i-decyl, n- or i-dodecyl, n- or i-octadecyl, alkyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl; furthermore represents cyclopropyl, cyclopropyhnethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, each of which is optionally monosubstituted to tetrasubstituted in the cycloalkyl moiety by identical or different substituents from the group consisting of fluorine, chlorine, bromine, methyl, ethyl, n- or i-propyl, chloromethyl, dichloromethyl or trifluoromethyl; furthermore represents phenylalkyl, phenylalkenyl, phenyl alkynyl, phenyl or naphthyl, each of which has, in the case of phenylalkyl, phenylalkenyl and phenylalkynyl, up to 6 carbon atoms in the straight-chain or branched alkyl or alkenyl or alkynyl moiety and each of which is optionally monosubstituted to trisubstituted in the aryl moiety by identical or different substituents, suitable aryl substituents in each case being: fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethytltio, trifluoromethyl, trifluoromethoxy, trifluoromethylthio, methylcarbonyl, ethylcarbonyl, methoxycarbonyl, ethoxycarbonyl, aminocarbonyl, N-methylaminocarbonyl, N,Ndmethylaminocarbonyl, N-ethylamino-carbonyl, NN-diethylaminocarbonyl, N-formylamino, N-acetylamino, N-methyl-N-formylamino, N-methyl-N-acetylamino, N-ethyl-N-formylamino, N-ethyl-N-acetylanuo, methoximinomethyl, methoximinoethyl, ethoximinomethyl, ethoximinoethyl, or phenyl which is optionally monosubstituted to trisubstituted by identical or different substituents from the group consisting of fluorine, chlorine, bromine, methyl and/or ethyl;

$R^9$ represents hydrogen, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dimethylaminomethyl, diethylanomethyl, dipropylaminomethyl, dimethylaminoethyl, diethylaminoethyl, dipropylaminoethyl, dimethylaminopropyl, diethylaminopropyl ordipropylaminopropyl; or $R^8$ and $R^9$ together with the nitrogen atom to which they are bonded represent a heterocycle of the formula

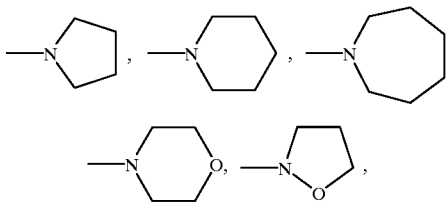

each of which is optionally monosubstituted, disubstituted or trisubstituted by methyl and/or ethyl and/or methoxycarbonyl and/or ethoxycarbonyl;

$R^4$, $R^5$, $R^6$ and $R^7$ independently of one another in each case represent hydrogen, fluorine, chlorine, bromine, cyano, nitro, methyl, ethyl, n- or i-propyl, n-, i-, s- or t-butyl, methoxy, ethoxy n- or i-propoxy, n-, i-, s- or t-butoxy, methylthio, ethylthio, trifluoromethyl, trifluoromethoxy or trifluoromethylthio. referred compounds of formula (II) are those compounds of formula (II) wherein $R^4$, $^5$, $R^6$ and $R^7$ are each hydrogen; $R^8$ is N-butyl, N-pentyl, N-n-hexyl, or N-cyclohexyl-methyl and $R^9$ is hydrogen; or wherein $R^8$ and $R^9$ are taken together with the nitrogen atom to which they are bonded forming a N-cyclohexyl.

The most preferred compound of formula (II) is N-cyclohexyl-benzothiophene-2-carboxamide-S,S-dioxide, referred to as "compound (2)" throughout the description, having the following structure:

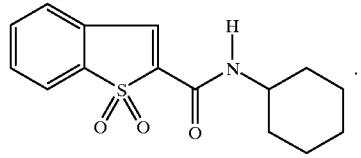

(2)

The active ingredients (I) and (II) may be present in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term salt form also comprises metal complexes which the basic components (I) or (II) may form. One of the components may occur as a complex and the other not; or both components may occur as a complex. Metal complexes as mentioned above consist of a complex formed between one or more molecules of the active ingredient and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminum, tin, lead as well as the first to the eighth transition groups of the periodical system such as, for example, chromium, manganese, iron, cobalt, nickel, copper, zinc and the like. Preferred are the metals pertaining to the transition elements of the fourth period. The metals may be present in each of their possible valences. The metal ions may be present in any of their possible valences, the most preferred metal copper being most advantageously used in its divalent form Cu(II). Suitable copper compounds are copper sulfate, acetate, hydroxide, oxide, borate, fluoride and in particular copper hydroxide carbonate $Cu(OH)_2CuCO_3$. The complexes can be mono- or polynuclear, they may contain one or more parts of the organic molecule as ligands.

The term salt as used hereinabove also comprises the solvates which the active ingredients of formula (I) and (II) are able to form. Examples of such solvates are e.g., the hydrates, alcoholates and the like.

The metal salt complexes of the active ingredients of formula (I) or (II) can conveniently be prepared by dissolving the metal salt in a suitable solvent e.g. ethanol, and adding thereto the active ingredients. The thus obtained complexes may be isolated following art-known techniques, e.g. by filtration or evaporation, and may be further purified , e.g. by recrystallization. The term salt as used hereinabove also comprises the solvates which the compounds of formula (I) or (II) are able to form, e.g. hydrates, alcoholates and the like.

The synergistic mixtures or compositions according to the present invention are most useful to combat wood-destroying and wood-discoloring fungi or prevent the growth thereof in wood or wood products. As wood which can be preserved with the synergistic compositions according to the present invention is considered, for example, wood products such as timber, lumber, railway sleepers, telephone poles, fences, wood coverings, wicker-work, windows and doors, plywood, particle board, waferboards, chipboard, joinery, bridges or wood products which are generally used in housebuilding, construction and carpentry. Synergistic compositions according to the present invention can also advantageously be applied in the cellulose and paper industry, in particular to protect pulpwood for paper manufacture from final attack; and also in biodegradable materials such as, for example, textiles of natural fibers, e.g. cotton, flax, hemp, wool, silk and the like; textiles of synthetic fibers, e.g. polyamide, polyacrylonitrile or polyester fibers, or of mixtures of such fibers; coatings, e.g. oil paints, dispersion paints, lacquers, lacquer films, whitewash, finishing stains and the like; glues and other such materials which are biodegradable by fungi.

The synergistic mixtures of the present invention are active against a broad range of fungi. As examples of such fungi there may be named Ascomycetes (e.g. Venturia, Podosphaera, Erysiphe, Monilinia, Uncinula, Aureobasidium, Scierophoma); Basidiomycetes (e.g. Hemileia, Rhizoctonia, Puccinia, Coniophora, Serpula, Poria, Uromyces, Gloeophyllum, Lentinus, Coniolus, Irpex); Fungi imperfecti (e.g. Botrytis, Helminthosporium, Rhynchosponium, Fusanium, Septoria, Cercospora, Alternaria, Pyricularia, Penicillium, Geotrichum).

Wood which is preserved from staining, discoloring and decay is meant to be protected from for example, moulding, rotting, loss of its useful mechanical properties such as breaking strength, resistance to shock and shearing strength, or decrease of its optical or other useful properties due to the occurrence of odor, staining and spot formation. These phenomena are caused by a number of micro-organisms of which the following are typical examples:

Wood-discoloring fungi:

1: Ascomycetes:

Ceratocystis e.g. *Ceratocystis minor.*

Aureobasidium e.g. *Aureobasidium pullulans*

Scierophoma e.g. *Scierophoma pithyophila*

Clidosporium e.g. *Cladosporium herbarum*

2: Deuteromycetes:

*Fungi imperfecti*

Aspergillus e.g. *Aspergillus niger*

Dactylium e.g. *Dactylium fusarioides*

Penicillium e.g. *P. brevicaule, P. variabile, P. funiculosum* or *P. glaucum*

Scopularia e.g. *Scopularia phycomyces*

Trichoderma e.g. *Trichoderma viride* or *Trichoderma lignorum.*

Alternaria e.g. *Alternaria tenius, Alternaria alternata*

3: Zygomycetes:

Mucor e.g. *Mucor spinorus.*

Wood-destroying fungi

1: Soft-rot Fungi:

Chaetomium e.g. *Ch. globosum* or *Ch alba-arenulum*

Humicola e.g. *Humicola grisea*

Petriella e.g. *Petriella setifera*

Trichurus e.g. *Trichurus spiralis.*

2: White and brown rot Fungi:

Coniophora e.g. *Coniophoraputeana*

Coriolus e.g. *Coriolus versicolor*

Donkioporia e.g. *Donkioporia expansa*

Glenospora e.g. *Glenospora graphii*

Gloeophyllum e.g. *Gl. abietinum, Gl adoratum, Gl. protactum, Gl. sepiarium* or *Gl. trabeum*

Lentinus e.g. *L. cyathiformes, L. edodes, L. lepideus, L. grinus* or *L squarrolosus*

Paxillus e.g. *Paxillus panuoides*

Pleurotus e.g. *Pleurotis ostreatus*

Poria e.g. *P. monticola, P. placenta, P. vailiantii* or *P. vaporaria*

Serpula (Merulius) e.g. *Serpula himantoides* or *Serpula lacrymans*

Stereum e.g. *Stereum hirsutum*

Trychophyton e.g. *Trychophyton mentagrophytes*

Tyromyces e.g. *Tyromyces palustris.*

In order to protect wood from decay it is treated with synergistic compositions according to the present invention. Such treatment is applied by several different procedures such as, for example, by treating the wood in closed pressure or vacuum systems, in thermal or dip systems and the like, or by a wide variety of surface treatments, e.g. by spraying, atomizing, dusting, scattering, pouring, brushing, dipping, soaking or impregnating the wood with a composition comprising a compound of formula (I), in particular 3-benzo[b]thien-2-yl)-5,6-dihydro-1,4,2-oxathiazine 4-oxide, or a salt thereof, and a compound of formula (II), in particular N-cyclohexylbenzothiophene-2-carboxamide-S,S-dioxide (II), or a salt thereof, in quantities producing a mutual synergistic effect, and a carrier.

The amount of each of the active ingredients of formula (I) and (II) in the compositions according to the present invention is such that a mutual synergistic fungicidal effect is obtained upon application. In particular, it is contemplated that in the compositions to be used directly, the concentration of a compound of formula (I), in particular 3-(benzo[b]thien-2-yl)-5,6-dihydro-1,4,2-oxathiazine, 4-oxide (i.e. compound 1), taken as base equivalent, may range from 10 to 5000 ppm, in particular from 50 to 2000 ppm or from 50 to 1000 ppm, more in particular from 100 to 800 ppm; and the concentration of the compound of formula (II), in particular N-cyclohexyl-benzothiophene-2-carboxamide-S,S-dioxide (i.e. compound 2), taken as base equivalent is contemplated to range from 10 to 5000 ppm, in particular from 50 to 2000 ppm or from 100 to 1000 ppm, more in particular from 200 to 800 ppm. In many instances said compositions to be used directly can be obtained from concentrates upon dilution with aqueous or organic media, such concentrates also being intended to be covered by the term composition as used in the definitions of the present invention. The content of the active ingredients in the above-indicated compositions is from 0.01 to 95%, preferably from 0.1 to 50% more preferably from 0.1 to 20% and in particular from 0.2 to 15% by weight. The compositions according to the invention are preferably used in the form of solutions or emulsions.

The ratio between the active ingredients of formula (I) and (II) will be such that a synergistic fingicidal effect is obtained with both active ingredients. Particularly, the weight ratio between (I) and (II) may range from 50:1 to 1:50, more particularly from 20:1 to 1:20 and preferably will range from about 5:1 to 1:5. When the compound of formula (I) is 3-(benzo[b]thien-2-yl)-5,6-dihydro-1,4,2-oxathiazine, 4-oxide (i.e. compound 1), and the compound of formula (II) is N-cyclohexyl-benzothiophene-2-carboxamide-S,S-dioxdde (i.e. compound 2), the weight ratio between (I) and (II) preferably ranges from 1:64 to 2:1, more particularly from 1:16 to 1:1 and preferably will be from 1:4 to 1:2.

The active ingredients of formula (I) and (II) are used in unmodified form or together with adjuvants conventionally employed in the art of formulation. The formulations, i.e. the compositions, preparations or mixtures containing the active ingredients and, where appropriate, a solid or liquid adjuvant, are prepared following art-known procedures, e.g. by homogeneously mixing and/or grinding the active ingredients with extenders, e.g. solvents, solid carriers and, where appropriate, surface-active compounds (surfactants), to emulsifiable concentrates, directly sprayable or dilutable solutions, dilute emulsions, wettable powders, soluble powders, dusts, granulates, and also encapsulations in e.g. polymer substances. Both the nature of the compositions and the methods of application such as spraying, atomizing, dusting, scattering or pouring, brushing, dipping, soaking or impregnating, should be chosen in accordance with the intended objectives and the prevailing circumstances. It is evident that in general different compositions with different characteristics will be required for use in plant protection on the one hand, and for use in material protection on the other. Carriers and adjuvants equally useful in both types of compositions are described first.

Appropriate carriers and adjuvants for use in the compositions of the present invention may be solid or liquid and correspond to suitable substances known in the art for preparing formulations for treating plants or the loci thereof, or for treating plant products, in particular for treating wood, such as, for example, natural or regenerated mineral substances, solvents, dispersants, surfactants, wetting agents, adhesives, thickeners, binders, fertilizers, anti-freeze agents, repellents, colour additives, corrosion inhibitors, water-repelling agents, siccatives, UV-stabihizrs and other active ingredients.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffms, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water, or a mixture of said solvents.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds. Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts. More frequently, however, so-called synthetic surfactants are used, especially fatty sulfonates, fatty sulfates, sulfonated benzimidazole derivatives or alkylaryl-sulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of suluric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene-sulfonic acid, dibutylnaphthalene-sulfonic acid, or of a naphthalene-sulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol polyethoxy-ethanols, castor oil polyglycol ethers, polypropylenelpolyethylene oxide adducts, tributylphenoxy-polyethoxyethanol, polyethylene glycol and octylphenoxypolyethoxyethanol. Fatty acid esters of polyethylene sorbitan, such as polyoxyethylene sorbitan trioleate, are also suitable non-ionic surfactants. They are of particular utility in compositions for material, in particular wood, protection.

Cationic surfactants are preferably quaternary ammonium salts wherein at least one N-substituent is a $C_8$–$C_{22}$alkyl radical and the further substituents are unsubstituted or halogenated lower alkyl, benzyl or hydroxy lower alkyl radicals. The salts are preferably in the form of halides, methylsulfates or ethylsulfates, e.g. stearyltrimethylanimonium chloride or benzyldi(2-chloroethyl)ethylammonium bromide. They are particularly useful in compositions for agrochemical purposes.

The surfactants customarily employed in the art of formulation are described e.g. in the following publications: "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

The following paragraphs in particular relate to compositions for use in plant protection. In general such compositions are designed so as to be innocuous to culture plants, to be easily and safely applicable, to have good bioavailability to the host plants and to remain (persist) only temporarily in the environment.

Particularly advantageous additives useful to improve the application and reduce the dose of the active ingredients, are the natural (animal or plant) or synthetic phospholipids of the cephalin or lecithin type such as, for example, phosphatidylethanolamine, phosphatidyl serine, phosphatidylglycerine, lysolecithin, or cardiolipin. Such phospholipids may be obtained from animal or plant cells, in particular from brain-, heart- or liver tissue, egg yolks or soy beans. Appropriate such phospholipids are for instance, phosphatidylcholine mixtures. Synthetic phospholipids are for instance, dioctanylphosphatidylcholine and dipalmitoylphosphatidylcholine.

In case of liquid formulations, and particularly of aqueous or alcoholic formulations, it is recommendable to add an appropriate surfactant, either from the anionic, cationic, nonionic or amphoteric type. In particular said surfactants will be of the cationic type and more in particular said surfactant is a quaternary ammonium salt or a mixture of quaternary ammonium salts. Such quaternary ammonium surfactants comprise, e.g., ammonium salts having four hydrocarbon radicals which may optionally be substituted with halo, phenyl, substituted phenyl or hydroxy; said hydrocarbon radicals in particular being alkyl or alkenyl radicals; they may also be derived from fatty acids or alcohols, e.g. cetyl, lauryl, palmityl, myristyl, oleyl and the like or from the hydrosylates form coconut oil, tallow oil, soy bean oiL or the hydrogenated forms thereof, and the like.

Examples of such quaternary ammonium salts are of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl alkyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

As used in the foregoing enumeration of quaternary ammonium salts, the terms "coco", "tallow" and "hydrogenated tallow" designate those hydrocarbon radicals derived from the hydrosylates of coconut oil, tallow oil or hydrogenated tallow oil. The weight ratio between said quaternary ammonium surfactants and the active ingredients of formula (I) and (II) is situated between 1:1 and 10:1. Excellent results are obtained when said ratio is about 5:1.

The following paragraphs in particular relate to compositions for use in wood protection. In general such compositions are designed so as to penetrate well in to wood, to persist there for a long time, and to be industrially applicable.

A biocidally active quaternary ammonium compound or tertiary amine salt can advantageously be used in the formulation of emulsions of the active ingredients of formula (I) and (II) in aqueous solutions of metal salts. Microemulsions may thus be formed which have particular utility in wood preservation. Additional advantages related to these adjuvants comprise their solubilizing effect on the active ingredients of formula (I) and (II), their contributory biocidal effect and their ability to promote penetration of the formulation into wood.

Binders are meant to comprise binding drying oils (e.g. linseed oil) and resins that are water-dilutable or dilutable, dispersible or emulsifiable in organic solvents, e.g. acryl, vinyl, polyester, polyurethane, alkyd, phenolic, hydrocarbon and silicon resins. Mixtures of an alkyd resin with a drying oil are advantageously used as a binding material. Part of the binding material may further be substituted with one or more fixing agents or one or more plasticizers. These adjuvants delay or prevent evaporation of the active ingredients as well precipitation or crystallisation thereof. About 0.01% to about 30% of the binding material may thus be replaced. Suitable plasticizers are phthalic acid esters, e.g. the dibutyl, dioctyl and benzylbutyl phthalate esters; phosphoric acid esters, e.g. tributylphosphate; fatty acid esters, e.g. di(2-ethylhexyl) adipate, butylstearate, amylstearate, butyloleate; glycerolethers; glycolethers; glycerolesters; and p-toluenesulfonic acid esters. Suitable fixing agents are polyvinylalkyl ethers, e.g. polyvinylmethyl ethers, or ketones, e.g. benzophenone or ethylenebenzophenone.

In view of their solubility in organic solvents the active ingredients are well suited for application in non-aqueous media, which is of interest in wood-preservation. The wood or wood products to be protected can easily be impregnated with such solutions. As organic solvents there may be used aliphatic and aromatic hydrocarbons, their chlorinated derivatives, acid amides, mineral oils, alcohols, ethers, glycolethers, such as, for example, methylene chloride, propylene glycol, methoxyethanol, ethoxyethanol, N,N-dimethylformamide and the like or mixtures of such solvents, to which there may be added dispersants or emulsifiers such as sulfated ricinus oil, fatty alcohol sulfates and other additives.

Particularly attractive formulations comprise water-dilutable wood-preservative liquids containing an appropriate amount of a suitable solvent, a suitable solubilizer and both the active ingredients. Preferably there is used 10–80% of a solvent, 20–80% of a solubilizer and from 0.01 to 10% of the active ingredients (I) and (II).

Preferred solubilizers to be used in the said water-dilutable wood-preservative liquids are selected from:

i) addition products of 1 to 60 moles of ethylene oxide with 1 mole of a phenol which is further substituted with at least one $C_{1-5}$alkyl group; and ii) addition products of 1 to 60 moles of ethylene oxide with 1 mole of ricinus oil.

The most preferred solubilizers are selected from:

i) addition products of 1 to 60 moles of ethylene oxide with 1 mole of nonylphenol or octylphenol; and ii) addition products of 1 to 60 moles of ethylene oxide with 1 mole of ricinus oil.

Said suitable solvent should fulfill the requirements of sufficiently solubilizing the active ingredients and, when combined with the solubilizer, of being homogeneously miscible with a predominantly aqueous medium. Preferred solvents are 2-butoxyethanol, butyl 2-hydroxyacetic acid ester and propyleneglycol monomethylether.

Preferred water-dilutable compositions for use in wood protection comprise active ingredients (I) and (II), a copper compound, suitable solvents and/or solubility enhancers and optionally other adjuvants. Suitable solvents are e.g. alcohols (ethanol, iso-propanol), glycols (ethylene and propylene glycol), glycolethers (ethylene glycol monomethyl and monoethyl ether), dimethylformamide, n-methylpyrrolidone, which yield homogenous concentrates. As solubilizers there may be employed carboxylic acids, or the amine, alkali metal or copper salt forms corresponding thereto, so that the amount of the organic solvent used in the homogenous concentrates can be kept to a minimum. Examples of such acids are propionic, hexanoic, heptanoic, 2-ethylhexanoic, iso-octanoic, sebacic, cyclohexanoic, benzoic, 3-hydroxybenzoic and 4-hydroxybenzoic acid. To improve further the industrial applicability of such water-dilutable, homogenous compositions comprising a carboxylic acid as solubilizer, advantageous use may be made of polyethyleneimines (PEI, Polymin) derived from ethyleneimine (aziridine) and having the formula $(C_2H_5N)_n$. The degree of polymerization 'n' should be larger than 10 and preferably ranges from about 50 to about 1000, and in particular is about 150. The use of alkanolamines, in particular monoethanolamine, but also di- and triethanolamine, as complexing agents for the copper compound employed may be of particular benefit. Typically there may be used about 4 molar equivalents of alkanolamine per mole of copper. Further useful additives are, for example, boron derivatives, e.g. boric acid, its salts and esters, and fluorides, e.g. potassium fluoride.

Water-dilutable homogenous concentrates in particular comprise by weight:
2.5 to 45%, in particular 10 to 20% copper compound,
5 to 50%, in particular 20 to 40% alkanolamine,
0.25 to 15%, in particular 1 to 10% of compounds of formula (I) and (II),
0.5 to 30%, in particular 5 to 15% surfactant(s),
15 0 to 40% other fungicidal compoundis),
0 to 40% organic solvent(s),
0 to 40% carboxylic acid(s), and
0 to 40% polymin.

Said water-dilutable wood-preserving liquids have the advantage that almost instantaneously homogeneous or quasi homogeneous solutions are formed by mixing these liquids with predominantly aqueous media These solutions have an extremely high physical stability, not only at ambient temperature, ie. at temperatures comprised between 15° C. and 35° C., but also at decreased temperatures. Thus, the physical stability of said solutions does not deteriorate after several freeze-thaw cycles. Said homogeneous solutions further unite the advantages of moistening the wood-surface well and penetrating the wood to a high degree, resulting in a high uptake of the solution and its active ingredients by the wood, and, consequently, obtaining the desired preservation of the treated wood. Additionally, due to a more uniform uptake of the aqueous solution the wood-preserving liquids and the resulting aqueous solutions are particularly useful in treatment techniques which require the possibility of a continuous process, such as, for example, impregnation or dip techniques. In addition, the solutions formed with the wood-preserving liquids unite in themselves the hereinabove mentioned advantages with those which are characteristic of predominantly aqueous media, such as, for example, a relatively high flashpoint and reduced toxicity, resulting in advantageous influence on the environment and the health and safety of the applicator, lack of irritation and the like benefits.

Apart from both the aforementioned active ingredients of formula (I) and (II), the compositions according to the present invention may further contain other active ingredients, e.g. other microbiocides, in particular insecticides, and also bactericides, acaricides, nematicides, herbicides, plant growth regulators, fertilizers or further fingicides. As antimicrobial agents, which may be used in combination with the active substances there may be considered products of the following classes : phenol derivatives such as 3,5-dichlorophenol, 2,5-dichlorophenol, 3,5-dibromophenol, 2,5-dibromophenol, 2,5-(resp. 3,5)-dichlorobromophenol, 3,4,5-trichlorophenol, tribromophenol, trtrachlorophenol, 3-methyl-4-chlorophenol; chlorinated hydroxydiphenylethers such as, for example, 2-hydroxy-3,2'4'-trichlorodiphenylether; phenylphenol (o-, m-, p-), 4-chloro-2-phenylphenol, 4chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; diiodomethyl-p-tolyl-sulfone, 3-iodo-2-propynyl-alkohol, 4-chlorophenyl-3-iodopropargyl-formal, 3-bromo-2,3-diiodo-2-propenylethylcarb-Rat, 2,3,3-triiodoalkylalkohol, 3-bromo-2,3-diiodo-2-propenylalkohol, 3-iodo-2-propynyl-n-butylcarbamate, 3-iodo-2-propynyl-n-hexylcarbamate, 3-iodo-2-propynyl-cyclohexylcarbamate, 3-iodo-2-propynyl-phenyl-carbamate; mono-, di- and polyamines such as dodecylamine or 1,10-di(n-heptyl)-1,10-diaminodecane; sulfonium- and phosphonium compounds; mercapto compounds as well as their alkali, earth alkaline and heavy metal salts such as 2-mercaptopyridine-N-oxide and its sodium, iron, manganese and zinc salt, 3-mercaptopyridazin-2-oxide, 2-mercaptoquinoxaline-1-oxide, 2-mercaptoquinoaline-i-N-oxide, as well as the symmetrical disulfides of said mercapto compounds; ureas such as tribromo- or trichlorocarbanilide, dichlorotrifluoromethyl-diphenylurea; tribromosalicylanilide; 2-bromo-2-nitro-1,3-dihydroxypropane (bronopol); dichlorobenzoxazolone; chlorohexidine; sulfenamides e.g. dichlofluanid, tolylfluanid, folpet, fluorfolpet; benzimidazoles e.g. carbendazim, benomyl, fuberidazole, thiabendazole; thiocyanates e.g. thiocyanatomethylthiobenzothiazole, methylenebisthiocyanate; quaternary ammonium compounds e.g. benzyldimethyltetradecyl ammonium chloride, benzyldimethyldodecyl ammonium chloride, didecyldimethyl ammonium chloride; morpholine derivates e.g. tridemorph, fenpropimorph, falimorph; azoles e.g. triadimefon, triadimenol, bitertanol, prochloraz; 2-(1-chlorocyclopropyl)-1-(2-chlorophenyl)3-(1H-1,2,4-triazol-1-yl)-propan-2-ol; isothiazolinones e.g. N-methylisothiazolin-3-one, 5-chloro-N-methyl-isothiazolin-3-one, 4,5-dichloro-N-octylisothiazolin-3-one, N-octyl-isothiazolin-3-one; benzisothiazolinone, cyclopenteneisothiazolinone; tetrachloro-4-methylsulfonyl-pyridine; metal salts e.g. tin, copper, zink naphthenate, ctoate, 2-ethylhexanoate, oleate, phosphate, benzoate; oxides e.g. tributyltin oxide, $Cu_2O$, CuO, ZnO; dialkyldithiocarbamate e.g. Na- and Zn-salts of dialkyldithio-carbamates, tetramethylthiuramdisulfide; nitriles e.g. 2,4,5,6-tetrachloroisophthalodinitrile; benzothiazole e.g. 2-mercaptobenzothiazole; quinolines e.g. 8-hydroxyquinoline and its Cu-salts; boron compounds e.g. boric acid, boric acid esters, borax; formaldehyde and formaldehyde releasing compounds e.g. benzylalkohol mono (poly)hemiformal oxazolidine, hexahydro-S-triazine, N-methylol-chloracetamide, parafotmaldehyde; tris-N-(cyclohexyldiazeniumdioxy)-aluminium, N-cyclohexyl-diazenium-dioxy)-tributyltin bis-N-(cyclohexyldiazeniumdioxy)-copper.

The compositions of the present invention comprising the aforementioned active ingredients of formula (I) and (II) may further comprise a fungicidally active triazole such as, for example, azaconazole (1-[[2-(2,4-dichlorophenyl)-1,3-dioxolan-2-yl]methyl]-1H-1,2,4-triazole), bromuconazole (1-[4-bromo-2-(2,4-dichloro-phenyl)tetrahydrofurfuryl]-1H-1,2,4-triazole), cyproconazole (α-(4-chlorophenyl)-α-(1-cyclopropylethyl)-1H-1,2,4-triazole-1-ethanol), difenoconazole (1-[2-[4-(4-chlorophenoxy)-2-chlorophenyl]-4-methyl-1,3-dioxolan-2-ylmethyl]-1H-1,2,4-triazole), epoxiconazole (1-[3-(2-chlorophenyl)-2-(4fluorophenyl)oxiran-2-ylmethyl]-1H-1,2,4-triazole), fenbuconazole (4-(4-chlorophenyl)-2-phenyl-2-(1H-1,2,4triazol-1-ylmethyl)-butyronitrile), hexaconazole (α-butyl-α-(2,4-dichlorophenyl)-1H-1,2,4-triazole-1-ethanol), metconazole (5-[(4-chlorophenyl)methyl]-2,2-dimethyl-1-(1H-1,2,4-triazol-1-ylmethyl)cyclopentanol), penconazole (1-[2-(2,4-dichlorophenyl)pentyl]-1H-1,2,4-triazole), propiconazole (1-[[2-(2,4-dichlorophenyl)-4-propyl-1,3-dioxolan-2-yl]methyl]-1H-1,2,4-triazole), tebuconazole (α-[2-(4-chlorophenyl)ethyl]-α-(1,1-dimethylethyl)-1H-1,2,4-triazol-1-ethanol), or triticonazole ((E)-5-(4-chlorophenyl)methylene)-2,2-dimethyl-1-(1H-1,2,4triazol-1-ylmethylI) cyclopentanol).

As insecticidal agents which may be used in the combination according to the present invention the following classes of products may be considered: insecticides having a natural origin, e.g., nicotine, rotenone, pyrethrum and the like; chlorinated hydrocarbons, e.g., lindane, chlordane, endosulfan and the like; organic phosphor compounds, e.g. azinphos-ethyl, azinphos-methyl, 1-(4-chlorphenyl)-4(O-ethyl, S-propyl)phosphoryl-oxypyrazole, chlorpyrifos, coumaphos, demeton, demeton-S-methyl, diazinon, dichlorvos, dimethoate, ethoprophos, etrimfos, fenitrothion, fenthion, heptenophos, parathion, parathionmethyl, phosalone, phoxim, piriniphos-ethyl, pirmiphos-methyl, profenofos, prothiofos, sulfprofos, triazophos, richlorphon; carbamates, e.g., aldicarb, bendiocarb, carbaryl, carbofuran, carbosulfan, cloethocarb, 2-(1-methylpropyl) phenylmethylcarbamate, butocarboxirme, butoxycarboxime, fenoxycarb, isoprocarb, methomyl, methiocarb, oxamyl, pirimicarb, promecarb, propoxur and thiodicarb; biological insecticides, e.g., products originating from *Bacillus thuringiensis*; synthetic pyrethroids, e.g., allethrin, alphamethrin, bioresmethrin, bifenthrin, cycloprothiin, cyfluthn, cyhalothrin, cypermeliin, decamethrin, deltamethrin, fenpropatIrn, fenfluthrin, fenvalerate, flucytlirinate, flumethrin, fluvalinate, halothrin, permethrn, resmethrin and tralomethrin, alpha-cyano-3-phenyl-2-methylbenzyl-2,2-dimethyl-3-(2-chloro-2-trifluoromethylvinyl)cyclopropancarboxylate; organosilicon compounds such as dimethylphenylsilylmethyl-3-phenoxybenzylethers e.g., dimethyl(4-ethoxyphenyl)-silylmethyl-3-phenoxybenzylether; or dimethylphenylsilylmethyl-2-phenoxy-6-pyridylmethylethers e.g. dimethyl(9-ethoxyphenyl) silylmethyl-2-phenoxy-6-pyridylmethylether or [(phenyl)-3-(3-phenoxyphenyl)propyl](dimethyl)silanes e.g. (4-ethoxyphenyl)[3-(4fluoro-3-phenoxyphenyl] propylldimethylsilane, silafluofen; nitroimines and nitromethylenes e.g. 1-(6-chloro-3-pyridinyhuethyl)-4,5-dihydro-N-nitro-1H-imidazol-2-amine (imidacloprid); benzoylureas e.g. lufenuron, hexaflumuron, flufenoxuron.

Particularly interesting active ingredients for combination with the present compositions comprising the active ingredients (I) and (II), in quantities producing a mutual synergistic effect, are: dichlofluanid, tolylfluanid, benzyldimethyldodecyl ammonium chloride, didecyldimethyl ammonium chloride, 3-bromo-2,3-diiodo-2-propenylalcohol, 3-iodo-2-propinyl-n-butylcarbamate, o-phenylphenol, m-phenylphenol, p-phenylphenol, 3-methyl-4-chorophenol, thiocyanatomethyl-thiobenzothiazole, N-methyl-isothiazolin-3-one, 5-chloro-N-methylisotiiazolin-3-one, 4,5-dichloro-N-octylisothiazolin-3-one, N-octyl-isothiazolin-3-one, benzylalkohol-mono(poly)hemiformal, N-methylolchloracetamide, phoxim, cyfluthrin, pennethrin, cypermethrin, deltamethrin, imidacloprid, silafluofen, lufenuron, bifenthrin, fenoxycarb, hexaflumuron, flufenoxuron.

Susceptible material (in particular wood) destroying insects are, for example:

| Beetles: |
| --- |
| *Anobium punctatum* |
| *Apate monachus* |
| *Bostrychus capucinus* |
| *Chlorophores pilosus* |
| *Dendrobium pertinex* |
| *Dinoderus minutus* |
| *Ernobius mollis* |
| *Heterobostrychus brunneus* |
| *Hylotrupes bajulus* |
| *Lyctus africanus* |
| *Lyctus brunneus* |
| *Lyctus linearis* |
| *Lyctus planicollis* |
| *Lyctus pubescens* |
| *Minthea rugicollis* |
| *Priobium carpini* |
| *Ptilinus pecticornis* |
| Sinoxylon spp. |
| *Trogoxylon aequale* |
| Tryptodendron spp. |
| *Xestobium rufovillosum* |
| Xyleborus spp. |
| Hymenoptera: |
| *Sirex juvencus* |
| *Urocerus augur* |
| *Urocerus gigas* |
| *Urocerus gigas taignus.* |
| Termites: |
| *Coptotermes formosanus* |
| *Cryptotermes brevis* |
| *Heterotermes indicola* |
| *Kalotermes flavicollis* |
| *Mastotermes darwiniensis* |
| *Reticulitermes flavipes* |
| *Reticulitermes lucifugus* |
| *Reticulitermes santonensis* |
| *Zootermopsis nevadensis.* |

The synergistic mixtures or compositions to be used directly may also be obtained from separate compositions containing the active ingredients or from the technical active ingredients themselves, by mixing and/or diluting with aqueous or organic media and/or optionally further adding adjuvants such as those described hereinabove. Said separate compositions generally are such as described hereinbefore for compositions containing both active ingredients. Of particular interest to some users may be preparation of custom-made formulations from both active ingredients in unmodified, technical form, thus allowing maximal flexibility in the application of the present synergistic mixtures of the active ingredients (I) and (II).

The present invention also concerns a method of combating fungi comprising treating plants or the loci thereof, or treating plant products such as wood; or pulpwood for paper manufacture, or treating biodegradable materials simultaneously, separately or sequentially with an effective amount of a synergistic, fungicidal composition as described hereinabove.

The present invention also concerns a method of preserving wood, wood products and biodegradable materials from deterioration by fungi. This method comprises the application to or incorporation in said wood or wood products or in or to said biodegradable materials, of a synergistic mixture or composition as defined hereinabove.

The active ingredients (I) and (II) can be applied to plants or to the loci thereof or to plant products, e.g. wood, or to biodegradable materials such as textiles, simultaneously, or can also be applied consecutively within a time period selected so that both active ingredients are allowed to act synergistically as antifungals, e.g. within 24 hours. In such applications, the active ingredients are used optionally together with adjuvants conventionally employed in the art of formulation such as carriers, surfactants or other useful additives. Therefore, the present invention also concerns products comprising a compound of formula (I), in particular 3-benzo[b]thien-2-yl)-5,6-dihydro-1,4,2-oxathiazine 4-oxide, or a salt thereof, and a compound of formula (II), in particular N-cyclohexylbenzo-thiophene-2-carboxamide-S,S-dioxide (II), or a salt thereof, as a combination for simultaneous, separate or sequential use in fungicidal applications. Such products may consists of a package comprising containers with both active ingredients, preferably in formulated form. Such formulated forms in general have the same composition as described for the formulations containing both active ingredients.

The following examples are intended to illustrate the scope of the present invention in all its aspects. Unless otherwise stated all parts therein are by weight.

A. BIOLOGICAL EXAMPLES

Example 1

The synergistic activity of the mixtures or compositions of (I) and (II) according to the present invention can be demonstrated by comparison with the activity of the active ingredients (I) and (II) alone. The efficacy of the active ingredients against mycelial growth and sporulation of *Aureobasidium pullulans, Aspergillus niger, Scierophoma entoxylina, Trichodenna viride*, was determined in the poison plate assay. The required concentrations of the fungicide (s) were obtained by diluting the active ingredients (I), (II) or the combination of (I) and (II) in dimethyl sulfoxide (DMSO) at 800 times the final test concentration. The stock solutions in DMSO were pipetted into Petri-dishes. Malt extract agar (3%) was added aseptically and uniform distribution was obtained by shaking. Each plate was spot inoculated with a spore or mycelial suspension. After incubation at 22° C. and 70% relative humidity for a period long enough to allow complete growth of controls, diameters of colonies were measured. Relative activities were calculated by taking the absence of fungal growth (diameter 0 mm) as 100%. From the activity of the active ingredients alone, the expected activities E were calculated by using the so-called formula of Colby: (Colby, S. R. Weeds 1967, 15: 20–22), $$E = X + Y - \frac{X \cdot Y}{100}$$

wherein X and Y express the relative activities obtained for each of the active ingredients. A synergistic effect can be acknowledged if the found activity exceeds calculated activity.

The results are listed in the tables 1 to 4 below and clearly demonstrate that the measured activity generally exceeds the calculated activity. Equal efficacy was observed whenever complete inhibition of fungal growth occurred by one of the active ingredients (I) or (II) alone. The compound of formula (I) used in the experiment was 3-benzo[b]-thien-2-yl)-5,6-dihydro-1,4,2-oxathiazine 4-oxide, i.e. compound (1). The compound of formula (II) used in the experiment was N-cyclohexyl-benzothiophene-2-carboxamide-S,S-dioxide, i.e. compound (2).

TABLE 1

Activity of compound (1) and compound (2) and their mixtures against *Aureobasidium pullulans*

| Conc. mg/l | | Experiment 1 Incubation period: 5 days | | | Experiment 2 Incubation period: 7 days | | |
|---|---|---|---|---|---|---|---|
| Co. No. | Co. No. | growth | activity % | | growth | activity % | |
| (1) | (2) | mm | measured | calculated | mm | measured | calculated |
| 0.62 | 0 | 33 | 13 | — | — | — | — |
| 1.25 | 0 | 26 | 32 | — | 44 | 8 | — |
| 2.50 | 0 | 15 | 61 | — | 38 | 21 | — |
| 5.00 | 0 | 5 | 87 | — | — | — | — |
| 0.62 | 2.5 | 29 | 24 | 20 | — | — | — |
| 1.25 | 2.5 | 22 | 42 | 37 | 42 | 13 | 10 |
| 2.5 | 2.5 | 13 | 66 | 64 | 35 | 27 | 22 |
| 5 | 2.5 | 6 | 84 | 88 | — | — | — |
| 0.62 | 5 | 27 | 29 | 27 | — | — | — |
| 1.25 | 5 | 19 | 50 | 42 | 38 | 21 | 14 |
| 2.5 | 5 | 9 | 76 | 67 | 32 | 33 | 26 |
| 5 | 5 | 5 | 87 | 87 | — | — | — |
| 0.62 | 10 | 22 | 42 | 59 | — | — | — |
| 1.25 | 10 | 14 | 63 | 57 | 32 | 33 | 16 |
| 2.5 | 10 | 6 | 84 | 75 | 26 | 46 | 27 |
| 5 | 10 | 5 | 87 | 92 | — | — | — |
| 0.62 | 20 | 16 | 58 | 59 | — | — | — |

TABLE 1-continued

Activity of compound (1) and compound (2) and their mixtures against *Aureobasidium pullulans*

| Conc. mg/l | | Experiment 1 Incubation period: 5 days | | | Experiment 2 Incubation period: 7 days | | |
|---|---|---|---|---|---|---|---|
| Co. No. (1) | Co. No. (2) | growth mm | activity % measured | calculated | growth mm | activity % measured | calculated |
| 1.25 | 20 | 10 | 74 | 68 | 21 | 56 | 29 |
| 2.5 | 20 | 5 | 87 | 81 | 12 | 75 | 39 |
| 5 | 20 | 5 | 87 | 94 | — | — | — |
| 0 | 2.5 | 35 | 8 | — | 47 | 2 | — |
| 0 | 5 | 32 | 16 | — | 45 | 6 | — |
| 0 | 10 | 24 | 37 | — | 44 | 8 | — |
| 0 | 20 | 18 | 53 | — | 37 | 23 | — |
| controls DMSO | | | 38 | | | 48 | |

TABLE 2

Activity of compound (1) and compound (2) and their mixtures against *Aspergillus niger.*

| Conc. mg/l | | Experiment 1 Incubation period: 5 days | | | Experiment 2 Incubation period: 7 days | | |
|---|---|---|---|---|---|---|---|
| Co. No. (1) | Co. No. (2) | growth mm | activity % measured | calculated | growth mm | activity % measured | calculated |
| 0.62 | 0 | 42 | 5 | — | — | — | — |
| 1.25 | 0 | 38 | 14 | — | 38 | 16 | — |
| 2.50 | 0 | 27 | 39 | — | 25 | 44 | — |
| 5.00 | 0 | 0 | 100 | — | — | — | — |
| 0.62 | 2.5 | 40 | 9 | 5 | — | — | — |
| 1.25 | 2.5 | 35 | 20 | 14 | 37 | 18 | 17 |
| 2.5 | 2.5 | 17 | 61 | 39 | 23 | 49 | 46 |
| 5 | 2.5 | 0 | 100 | 100 | — | — | — |
| 0.62 | 5 | 39 | 11 | 9 | — | — | — |
| 1.25 | 5 | 32 | 27 | 18 | 36 | 20 | 17 |
| 2.5 | 5 | 15 | 66 | 41 | 22 | 51 | 46 |
| 5 | 5 | 0 | 100 | 100 | — | — | — |
| 0.62 | 10 | 33 | 25 | 72 | — | — | — |
| 1.25 | 10 | 30 | 32 | 33 | 30 | 33 | 23 |
| 2.5 | 10 | 8 | 82 | 53 | 7 | 84 | 49 |
| 5 | 10 | 0 | 100 | 100 | — | — | — |
| 0.62 | 20 | 17 | 61 | 72 | — | — | — |
| 1.25 | 20 | 2 | 95 | 74 | 18 | 60 | 46 |
| 2.5 | 20 | 0 | 100 | 82 | 0 | 100 | 64 |
| 5 | 20 | 0 | 100 | 100 | — | — | — |
| 0 | 2.5 | 44 | 0 | — | 44 | 2 | — |
| 0 | 5 | 42 | 5 | — | 44 | 2 | — |
| 0 | 10 | 34 | 23 | — | 41 | 9 | — |
| 0 | 20 | 13 | 70 | — | 29 | 36 | — |
| controls DMSO | | | 44 | | | 45 | |

TABLE 3

Activity of compound (1) and compound (2) and their mixtures against *Sclerophoma entoxylina.*

| Conc. mg/l | | Experiment 1 Incubation period: 5 days | | | Experiment 2 Incubation period: 7 days | | |
|---|---|---|---|---|---|---|---|
| Co. No. (1) | Co. No. (2) | growth mm | activity % measured | calculated | growth mm | activity % measured | calculated |
| 0.62 | 0 | 42 | 2 | — | — | — | — |
| 1.25 | 0 | 37 | 14 | — | 47 | 4 | — |
| 2.50 | 0 | 27 | 37 | — | 40 | 18 | — |
| 5.00 | 0 | 7 | 84 | — | — | — | — |
| 0.62 | 2.5 | 37 | 14 | 9 | — | — | — |

TABLE 3-continued

Activity of compound (1) and compound (2) and their mixtures against *Sclerophoma entoxylina.*

| Conc. mg/l | | Experiment 1<br>Incubation period: 5 days | | | Experiment 2<br>Incubation period: 7 days | | |
|---|---|---|---|---|---|---|---|
| Co. No.<br>(1) | Co. No.<br>(2) | growth<br>mm | activity %<br>measured | calculated | growth<br>mm | activity %<br>measured | calculated |
| 1.25 | 2.5 | 34 | 21 | 20 | 45 | 8 | 6 |
| 2.5 | 2.5 | 21 | 51 | 42 | 33 | 33 | 20 |
| 5 | 2.5 | 6 | 86 | 85 | — | — | — |
| 0.62 | 5 | 37 | 14 | 18 | — | — | — |
| 1.25 | 5 | 35 | 19 | 28 | 45 | 8 | 8 |
| 2.5 | 5 | 22 | 49 | 47 | 32 | 35 | 22 |
| 5 | 5 | 5 | 88 | 88 | — | — | — |
| 0.62 | 10 | 30 | 30 | 41 | — | — | — |
| 1.25 | 10 | 27 | 37 | 30 | 38 | 22 | 20 |
| 2.5 | 10 | 19 | 56 | 49 | 22 | 55 | 32 |
| 5 | 10 | 4 | 91 | 87 | — | — | — |
| 0.62 | 20 | 22 | 49 | 41 | — | — | — |
| 1.25 | 20 | 18 | 58 | 48 | 27 | 45 | 31 |
| 2.5 | 20 | 9 | 79 | 62 | 15 | 69 | 42 |
| 5 | 20 | 5 | 88 | 90 | — | — | — |
| 0 | 2.5 | 40 | 7 | — | 48 | 2 | — |
| 0 | 5 | 36 | 16 | — | 47 | 4 | — |
| 0 | 10 | 35 | 19 | — | 41 | 16 | — |
| 0 | 20 | 26 | 40 | — | 35 | 29 | — |
| controls DMSO | | | 43 | | | 49 | |

TABLE 4

Activity of compound (1) and compound (2) and their mixtures against *Trichoderma viride.*

| Conc. mg/l | | Experiment 1<br>Incubation period: 5 days | | | Experiment 2<br>Incubation period: 7 days | | |
|---|---|---|---|---|---|---|---|
| Co. No.<br>(1) | Co. No.<br>(2) | growth<br>mm | activity %<br>measured | calculated | growth<br>mm | activity %<br>measured | calculated |
| 0.62 | 0 | 49 | 0 | — | — | — | — |
| 1.25 | 0 | 49 | 0 | — | 43 | 12 | — |
| 2.50 | 0 | 48 | 2 | — | 35 | 29 | — |
| 5.00 | 0 | 35 | 29 | — | — | — | — |
| 0.62 | 2.5 | 49 | 0 | 0 | — | — | — |
| 1.25 | 2.5 | 49 | 0 | 0 | 40 | 18 | 12 |
| 2.5 | 2.5 | 42 | 14 | 2 | 34 | 31 | 29 |
| 5 | 2.5 | 36 | 27 | 29 | — | — | — |
| 0.62 | 5 | 49 | 0 | 0 | — | — | — |
| 1.25 | 5 | 49 | 0 | 0 | 39 | 20 | 12 |
| 2.5 | 5 | 43 | 12 | 2 | 33 | 33 | 29 |
| 5 | 5 | 33 | 33 | 27 | — | — | — |
| 0.62 | 10 | 48 | 2 | 14 | — | — | — |
| 1.25 | 10 | 45 | 8 | 0 | 36 | 27 | 19 |
| 2.5 | 10 | 40 | 18 | 2 | 27 | 45 | 34 |
| 5 | 10 | 30 | 39 | 29 | — | — | — |
| 0.62 | 20 | 39 | 20 | 14 | — | — | — |
| 1.25 | 20 | 36 | 27 | 14 | 31 | 37 | 34 |
| 2.5 | 20 | 29 | 41 | 16 | 12 | 76 | 46 |
| 5 | 20 | 22 | 55 | 39 | — | — | — |
| 0 | 2.5 | 49 | 0 | — | 49 | 0 | — |
| 0 | 5 | 49 | 0 | — | 49 | 0 | — |
| 0 | 10 | 49 | 0 | — | 45 | 8 | — |
| 0 | 20 | 42 | 14 | — | 37 | 24 | — |
| controls DMSO | | | 49 | | | 49 | |

Example 2

The synergistic activity of the mixtures or compositions comprising a compound of formula (O) and a compound of formula (II) according to the present invention can be demonstrated by comparison with the activity of the active ingredients (I) and (II) alone in preventing destruction of wood by fungi versus the efficacy of either active ingredient alone was tested in a wood stick test with *Aureobasidium pullulans, Aspergillus niger, Penicillium purpurogenum* and *Scierophoma entoxylina* as test fungi. Oven-dried wood sticks (50×12×2 mm) of Scots Pine (*Pinus sylvestris*) were dipped during 3 hours in a methanol solution comprising a compound of formula (I), a compound of formula (II), or a combination of a compound of formula (I) and a compound of formula (II), and allowed to dry overnight in a sterile laminar air flow. In each Petri dish one stick was placed on culture medium, PDA PS (Potato Dextrose Agar containing 60 mg penicillin and 200 mg streptomycin), previously seeded with inoculum. Two drops of fungal or spore suspension were pipetted on the upper surface of the stick The Petri dishes were incubated at 22° C. and 70% relative humidity. The test was evaluated after sufficient growth of the fungus on the control sticks. The following score system was used:
0: sticks free of fungal growth
1: traces of growth on the stick
2: slight growth (5 to 25% of the surface covered)
3 : moderate growth (25 to 50% of the surface covered)
4: vigorous to maximum growth (more tha 50% covered)

To calculate synergism results were converted to the next artificial activities:
0: 100% activity
1: 95% activity
2: 75% activity
3: 50% activity
4: 0% activity Yhe expected activities E were calculated by using the so-called formula of Colby: (Colby, S. R. Weeds 1967, 15: 20–22), $$E = X + Y - \frac{X \cdot Y}{100}$$

wherein X and Y express the relative activities obtained for each of the active ingredients. A synergistic effect can be acknowledged if the found activity exceeds calculated activity.

The compound of formula (I) used in the experiment was 3-benzo[b]-thien-2-yl)-5,6-dihydro-1,4,2-oxathiazine 4-oxide, i.e. compound (1). The compound of formula (II) used in the experiment was N-cyclohexyl-benzothiophene-2-carboxamide-S,S-dioxide, i.e. compound (2).

TABLE 5

Synergistic effects between compound (1) and compound (2) on Aureobasidium in a stick test.

| compound (1) in ppm | compound (2) in ppm | stick test scores | % overgrown of the sticks | measured (relative) activity % | calculated (expected) activity % |
|---|---|---|---|---|---|
| 200 | 0 | 4 | 100 | 0 | — |
| 400 | 0 | 3 | 50 | 50 | — |
| 0 | 200 | 4 | 100 | 0 | — |
| 0 | 400 | 2 | 25 | 75 | — |
| 0 | 800 | 1 | 5 | 95 | — |
| 200 | 200 | 3 | 50 | 50 | 0 |
| 200 | 400 | 1 | 5 | 95 | 75 |
| 200 | 800 | 1 | 5 | 95 | 95 |
| 400 | 400 | 0 | 0 | 100 | 88 |
| 400 | 800 | 0 | 0 | 100 | 98 |
| control DMSO | | 4 | 100 | 0 | — |

TABLE 6

Synergistic effects between compound (1) and compound (2) on Aspergillus in a stick test.

| compound (1) in ppm | compound (2) in ppm | stick test scores | % overgrown of the sticks | measured (relative) activity % | calculated (expected) activity % |
|---|---|---|---|---|---|
| 200 | 0 | 4 | 100 | 0 | — |
| 400 | 0 | 3 | 50 | 50 | — |
| 0 | 200 | 4 | 100 | 0 | — |
| 0 | 400 | 4 | 100 | 0 | — |
| 0 | 800 | 4 | 100 | 0 | — |
| 200 | 200 | 4 | 100 | 0 | 0 |
| 200 | 400 | 3 | 50 | 50 | 0 |
| 200 | 800 | 3 | 50 | 50 | 0 |
| 400 | 400 | 3 | 50 | 50 | 50 |
| 400 | 800 | 3 | 50 | 50 | 50 |
| control DMSO | | 4 | 100 | 0 | — |

TABLE 7

Synergistic effects between compound (1) and compound (2) on Penicillium in a stick test.

| compound (1) in ppm | compound (2) in ppm | stick test scores | % overgrown of the sticks | measured (relative) activity % | calculated (expected) activity % |
|---|---|---|---|---|---|
| 200 | 0 | 4 | 100 | 0 | — |
| 400 | 0 | 2 | 25 | 75 | — |
| 0 | 200 | 4 | 100 | 0 | — |
| 0 | 400 | 3 | 50 | 50 | — |
| 0 | 800 | 2 | 25 | 75 | — |
| 200 | 200 | 4 | 100 | 0 | 0 |
| 200 | 400 | 2 | 25 | 75 | 50 |
| 200 | 800 | 1 | 5 | 95 | 75 |
| 400 | 400 | 2 | 25 | 75 | 88 |
| 400 | 800 | 1 | 5 | 95 | 94 |
| control DMSO | | 4 | 100 | 0 | |

TABLE 8

Synergistic effects between compound (1) and compound (2) on Sclerophoma in a stick test.

| compound (1) in ppm | compound (2) in ppm | stick test scores | % overgrown of the sticks | measured (relative) activity % | calculated (expected) activity % |
|---|---|---|---|---|---|
| 200 | 0 | 4 | 100 | 0 | — |
| 400 | 0 | 3 | 50 | 50 | — |
| 0 | 200 | 4 | 100 | 0 | — |
| 0 | 400 | 4 | 100 | 0 | — |
| 0 | 800 | 2 | 25 | 75 | — |
| 200 | 200 | 4 | 100 | 0 | 0 |
| 200 | 400 | 4 | 100 | 0 | 0 |
| 200 | 800 | 0 | 0 | 100 | 75 |
| 400 | 400 | 1 | 5 | 95 | 50 |
| 400 | 800 | 0 | 0 | 100 | 88 |
| Control DMSO | | 4 | 100 | 0 | |

What is claimed is:

1. A composition comprising the compound 3-(benzo[b]thien-2-yl)-5,6-dihydro-1,4,2-oxathiazine,4-oxide, or a salt form thereof, and the compound N-cyclohexylbenzothiophene-2-carboxamide-S,S,-dioxide, or a salt form thereof in quantities producing a synergistic fungicidal effect, and a carrier.

2. A composition according to claim 1 wherein the ratio by weight between the compound of formula (I) and the compound of formula (II) is from 50:1 to 1:50.

3. A composition according to claim 1 wherein the ratio by weight between the compound of formula (I) and the compound of formula (II) is from 10:1 to 1:10.

4. A composition according to claim 1 wherein the ratio by weight between the compound of formula (I) and the compound of formula (II) is from 1:4 to 1:2.

5. A composition according to claim 1 further comprising a copper compound.

6. A composition according to claim 1 further comprising a fungicidally active triazole.

7. A method for protecting wood, wood products, biodegradable materials or coatings comprising applying a composition of claim 1 to said wood, wood products, biodegradable materials or coatings.

8. A product containing the compound 3-(benzo[b]thien-)-yl-5,6,-dihydro-1,4,2-oxathiazine, 4-oxide, or a salt thereof, and the compound N-cyclohexylbenzothiophene or a salt thereof, as a combination for simultaneous, separate or sequential use in fungicidal applications.

* * * * *